US006835401B2

(12) United States Patent
Soldati

(10) Patent No.: US 6,835,401 B2
(45) Date of Patent: Dec. 28, 2004

(54) METHOD OF TREATING DISEASES CAUSED BY OVER-PRODUCTION OF FREE-RADICALS

(75) Inventor: Fabio Soldati, Savosa (CH)

(73) Assignee: Pharmaton SA, Bioggio (CH)

( * ) Notice: Subject to any disclaimer, the term of this patent is extended or adjusted under 35 U.S.C. 154(b) by 0 days.

(21) Appl. No.: 10/617,838

(22) Filed: Jul. 14, 2003

(65) Prior Publication Data

US 2004/0009248 A1 Jan. 15, 2004

Related U.S. Application Data

(62) Division of application No. 09/863,768, filed on May 24, 2001, now Pat. No. 6,627,231.
(60) Provisional application No. 60/206,945, filed on May 25, 2000.

(51) Int. Cl.$^7$ ........................ A61K 35/78; A61K 33/04; A01N 25/00; A01N 59/02
(52) U.S. Cl. ........................ 424/766; 424/702; 424/725; 424/768; 514/824
(58) Field of Search ................................ 424/702, 725, 424/766, 768; 514/824

(56) References Cited

U.S. PATENT DOCUMENTS

| 5,648,377 A | 7/1997 | Bombardelli et al. |
| 6,090,414 A | 7/2000 | Passwater et al. |
| 6,627,231 B2 | 9/2003 | Soldati |

FOREIGN PATENT DOCUMENTS

| EP | 0 712 630 A2 | 5/1996 |
| FR | 2 792 831 | 4/1999 |
| FR | 2 799 345 | 10/1999 |
| WO | WO 98/33494 | 8/1998 |
| WO | WO 98/57622 | 12/1998 |
| WO | WO 99/48386 | 3/1999 |

OTHER PUBLICATIONS

Baldi, A., et al., "The Relative Antioxidant Potencies of Some Polyphenols in Grapes and Wines," in *Wine: Nutritional and Therapeutic Benefits*, Chapter 13, ACS Symposium Series 661, Watkins, T.R., ed., American Chemical Society, Washington, DC, pp. 166–179 (1997).

Bisson, L.F., "Metabolic Syndrome X and the French Paradox," in *Wine: Nutritional and Therapeutic Benefits*, Chapter 14, ACS Symposium Series 661, Watkins, T.R., ed., American Chemical Society, Washington, DC, pp. 180–195 (1997).

Böhm, F., et al., "β–Carotene with vitamins E and C offers synergistic cell protection against $NO_x$," *FEBS Lett.* 436:387–389, Federation of European Biochemical Societies (1998).

Comstock, G.W., et al., "The Risk of Developing Lung Cancer Associated with Antioxidants in the Blood: Ascorbic Acid, Carotenoids, α–Tocopherol, Selenium, and Total Peroxyl Radical Absorbing Capacity," *Cancer Epidemiol. Biomarkers Prev.* 6:907–916, American Association for Cancer Research and the American Society of Preventive Oncology (1997).

Dreosti, I.E., "Nutrition, Cancer, and Aging," in: *Towards Prolongation of the Healthy Life Span: Practical Approaches to Intervention*, vol. 854, Harman, D., et al., eds., Annals of the New York Academy of Sciences, New York, pp. 371–377 (1998).

Ebeler, S.E., et al., "An In Vivo Experimental Protocol for Identifying and Evaluating Dietary Factors That Delay Tumor Onset: Effect of Red Wine Solids," in *Wine: Nutritional and Therapeutic Benefits*, Chapter 16, ACS Symposium Series 661, Watkins, T.R., ed., American Chemical Society, Washington, DC, pp. 215–229 (1997).

Fenech, M., "Chromosomal Damage Rate, Aging, and Diet," in *Towards Prolongation of the Healthy Life Span: Practical Approaches to Intervention*, vol. 854, Harman, D., et al., eds., Annals of the New York Academy of Sciences, New York, pp. 23–36 (1998).

Fuhrman, B., et al., "Lycopene Synergistically Inhibits LDL Oxidation in Combination with Vitamin E, Glabridin, Rosmarinic Acid, Carnosic Acid, or Garlic," *Antioxid. Redox Signal.* 2:491–506, Mary Ann Liebert, Inc. (Oct. 2000).

Fuhrman, B., et al., "Tomato lycopene and β–carotene inhibit low–density lipoprotein oxidation and this effect depends on the lipoprotein vitamin E content," *Nutr. Metab. Cardiovasc. Dis.* 7:433–443, Medikal Press (1997).

German, J.B., et al., "Wine Phenolics and Targets of Chronic Disease," in *Wine: Nutritional and Therapeutic Benefits*, Chapter 15, ACS Symposium Series 661, Watkins, T.R., ed., American Chemical Society, Washington, DC, pp. 196–214 (1997).

Krinsky, N.I., "The Antioxidant and Biological Properties of the Carotenoids," in *Towards Prolongation of the Healthy Life Span: Practical Approaches to Intervention*, vol. 854, Harman, D., et al., eds., Annals of the New York Academy of Sciences, New York, pp. 443–447 (1998).

(List continued on next page.)

Primary Examiner—David Naff
Assistant Examiner—Kailash C. Srivastava
(74) Attorney, Agent, or Firm—Sterne, Kessler, Goldstein & Fox P.L.L.C.

(57) ABSTRACT

The invention relates to a method for improving the cell protection which comprises the administration of a combination of the extracts of the plants *Vitis vinifera* and *Lycopersicon esculentum* with the vitamins C, E, beta-carotene and optionally selenium. Said combination can be used in the prevention of phatological conditions related in part to an overproduction of free radicals like aging, arteriosclerosis and cancer.

10 Claims, 10 Drawing Sheets

OTHER PUBLICATIONS

Maffei Facino, R., et al., "Free Radicals Scavenging Action and Anti–enzyme Activities of Procyanidines from *Vitis vinifera,*" *Arzneim.–Forsch./Drug Res.* 44 (I):592–601, Editio Cantor Verlag (1994).

Maxwell, S.R.J., "Wine Antioxidants and Their Impact on Antioxidant Activity In Vivo," in: *Wine: Nutritional and Therapeutic Benefits*, Chapter 12, ACS Symposium Series 661, Watkins, T.R., ed., American Chemical Society, Washington, DC, pp. 150–165 (1997).

Meydani, M., et al., "The Effect of Long–term Dietary Supplementation with Antioxidants," in *Towards Prolongation of the Healthy Life Span: Practical Approaches to Intervention*, vol. 854, Harman, D., et al., eds., Annals of the New York Academy of Sciences, New York, pp. 352–360 (1998).

Pastori, M., et al., "Lycopene in Association with α–Tocopherol Inhibits at Physiological Concentrations Proliferation of Prostate Carcinoma Cells," *Biochem. Biophys. Res. Commun.* 250:582–585, Academic Press (1998).

Renaud, S.C., et al., "Alcohol and Mortality in Middle–Aged Men from Eastern France," *Epidemiology* 9:184–188, Epidemiology Resources Inc. (1998).

Reiter, R.J., "Roundtable Discussion: How Best to Ensure Daily Intake of Antioxidants (from the Diet and Supplements) That is Optimal for Life Span, Disease, and General Health," in *Towards Prolongation of the Healthy Life Span: Practical Approaches to Intervention*, vol. 854, Harman, D., et al., eds., Annals of the New York Academy of Sciences, New York, pp. 463–476 (1998).

Stähelin, H.B., "The Impact of Antioxidants on Chronic Disease in Aging and in Old Age," *Int. J. Vitamin Nutr. Res.* 69:146–149, Hogrefe & Huber Publishers (May 1999).

Watkins, T.R., "Wine: Yesterday's Antidote for Today's Oxygen Stress," in *Wine: Nutritional and Therapeutic Benefits*, Chapter 1, ACS Symposium Series 661, Watkins, T.R., ed., American Chemical Society, Washington, DC, pp. 2–5 (1997).

International Search Report for International Application No. PCT/EP 01/05841, mailed Aug. 16, 2002.

Dialog File 351, Accession No. 10743551, Derwent WPI English language abstract for EP 0 712 630 A2.

Dialog File 351, Accession No. 13549806, Derwent WPI English language abstract for FR 2 792 831 A1.

Dialog File 351, Accession No. 13789398, Derwent WPI English language abstract for FR 2 799 345.

ANOVA, Tukey's post test:

Yeast (L), Yeast (H), Selenite (H), Selenite (L) vs Control p<0.001
Yeast (L) vs Yeast (H) p<0.001

Legend:
Yeast (L):   Selenium yeast (3.95 µg/ml): 50 nM Se
Yeast (H):   Selenium yeast (39.5 µg/ml): 500 nM Se
Selenite (L):   $Na_2SeO_3$ 50 nM
Selenite (H):   $Na_2SeO_3$ 500 nM ANOVA, Tukey's post test:

Yeast (H), Selenite (H), Selenite (L) vs Control p<0.001
Yeast (L) vs Control p<0.01

Legend:
Yeast (L):     Selenium yeast (3.95 µg/ml): 50 nM Se
Yeast (H):     Selenium yeast (39.5 µg/ml): 500 nM Se
Selenite (L):  $Na_2SeO_3$ 50 nM
Selenite (H):  $Na_2SeO_3$ 500 nM

METHOD OF TREATING DISEASES CAUSED BY OVER-PRODUCTION OF FREE-RADICALS

CROSS REFERENCE TO RELATED APPLICATIONS

The present application is a divisional of U.S. patent application Ser. No. 09/863,768, Filed on May 24, 2001, now U.S. Pat. No. 6,627,231, which claims benefit of the filing date of U.S. appl. No. 60/206,945, filed May 25, 2000, the disclosures of which are incorporated herein in entirety by reference.

BACKGROUND OF THE INVENTION

1. Field of the Invention

The present invention is related to a novel method of improving the cell protection, which utilises the administration of the combination of the extracts of the plants *Vitis vinifera* and *Lycopersicon esculentum* with the vitamins C, E, beta-carotene and selenium, as well as the use of such combination for treating or preventing pathologies related to an overproduction of free radicals like aging, arteriosclerosis and cancer.

2. Background Art

Antioxidants act to protect components of the body against free radical damage (Harman D.; Holliday R. and M. Meydany—Editor, "Towards Prolongation of healthy life span", Annals of the New York Academy of Sciences, Vol. 854, 1998, New York; Stäh:in H. B., "The Impact of Antioxidants on Chronic Disease in Aging and Old Age", Int. J. Vitamin. Nutr. Res. 69, 146–149, 1999).

Several epidemiological studies support the observation that an increase in antioxidant intake limits the clinical expression of coronary artery diseases and some tumours (Comstock G W; Alberg A J; Huang H Y, Wu K.; Burke A E; Hoffman S C; Norkus E P; Gross M.; Cutler R G; Morris J S; Spate V L; Helzlsouer K J, "The risk of developing lung cancer associated with antioxidants in the blood: ascorbic acid, carotenoids, alpha-tocopherol, selenium, and total peroxyl radical absorbing capacity", Cancer Epidemiol Biomarkers Prev 6, 907–916, 1997). Individuals with high dietary intakes of antioxidants may have a greater life expectancy.

Individual conditions, environmental stress and oxidative stress induced by environmental and nutritional factors exert its influence on a wide variety of individuals with varying defense capacities.

In general terms, individuals with very well balanced defense mechanisms will remain free of chronic disease, but will eventually succumb to the overall aging processes. Much more likely, however, is the case where critical systems are insufficiently protected and become injured. The sequence of this process will be clinically diagnosed as chronic disease.

Antioxidants as important elements in the body's defense against oxidative stress thus have a general anti-aging property as well as a specific disease-protective function. Since the consequences of chronic disease are among the leading causes of disability in old age, primary prevention by adequate antioxidative defense has not only an "anti-aging" function, but more importantly, a specific chronic-disease-preventing function. However, it becomes clear that this is a life-long important protective mechanism: primary prevention of age-related chronic diseases has to start early in life and needs to be continued throughout the whole life span.

The relationship between antioxidants and chronic disease is probably best investigated in cardiovascular disease. A strong inverse relationship between plasma antioxidant concentration, morbidity, and mortality from coronary heart disease was demonstrated. The analyses of the data allowed to quantify the contribution of the different antioxidative vitamins. According to these results a sufficient intake of vitamin E is most important, followed by vitamin C and carotene intake.

In the analysis of a population with an overall very good vitamin E status, a strong effect of vitamin C and beta-carotene was observed. It is quite well known that other antioxidants without vitamin functions originating from food, such as flavonoids, polyphenols, or lycopene have very important antioxidative functions (Fuhrman B.; Ben-Yaish L.; Attias J.; Hayek T.; Avaram M., "Tomato lycopene and beta-carotene inhibit low-density lipoprotein oxidation and this effect depends on the lipoprotein vitamin E content", Nutr. Metab. Cardiovasc. Dis. 7, 433–443, 1997; Pastori M.; Pfander H.; Boscoboinik D.; Azzi A., "Lycopene in association with alpha-tocopherol inhibits at physiological concentrations proliferation of prostate carcinoma cells", Biochem. Biophys. Res. Commun. 250 (3), 582–585, 1998; Boehm F.; Edge R.; McGarvey D J; Truscott T G, "Beta-carotene with vitamins E and C offers synergistic cell protection against Nox", FEBS Lett. 436, 387–389, 1998; Watkins T. R.—Editor, "Wine, Nutritional and Therapeutic Benefits", American Chemical Society Symposium Series 661, 1997, Washington D.C.).

In late adulthood and early old age, cancer is the leading cause of premature death. There is no question that a large majority of cancers are the result of environmental factors challenging the specific genetic endowment of tissue at high risk for proliferative disorders. Epidemiological evidence clearly demonstrates that a low intake of fruit and vegetables and low plasma concentrations of antioxidative vitamins correlated with a significantly elevated cancer morbidity and mortality. This holds true for gastrointestinal cancer and lung cancer, but also for prostate cancer and for breast cancer.

The neoplastic process is a highly complex sequence of events. Many potentially dangerous mutations occur continuously. Once these genetic changes have escaped the initial defense and repair mechanisms, these altered cells have to be eliminated by other defense mechanisms. One important mechanism is the apoptotic process. It may be that committed cells in the proliferative stage are protected by antioxidants against the body's own immune and apoptotic defense mechanisms. This might explain why antioxidants occur in higher concentration in breast cancer tissue. There is no doubt that a life-long high intake of a diet rich in fruit and vegetables and high in a variety of antioxidants substantially and significantly lowers the risk of malignant disorders in later life.

Primary degenerative brain disease and diseases related to cerebral vascular disturbances are the leading cause of disability in old age. Loss of autonomy, dependence and high social costs for individuals and society are the consequences of brain dysfunction. The impressive gain in individual life expectancy is overshadowed by the loss of mental function in old age. Hence, prevention and treatment of disorders leading to mental impairment have emerged as major challenge of the modern health care system. As in the previous examples, a combination of age-related functional changes superimposed by disorders of circulation or of certain neuronal systems leading to distinct chronic diseases are being observed.

Given the importance of antioxidants in the maintenance of cell integrity and cell function, antioxidants (vitamin E, carotenes, vitamin C) and other micronutrients from the food, e.g. polyphenols, flavonoids, lycopene, may decrease the risk of vascular disease, protect the neurons against oxidative stress and thus maintain neuronal function. Several epidemiological studies in elderly people have revealed a correlation between antioxidants and cognitive performance.

Other epidemiological data have shown that red wine may reduce the mortality rate from heart disease, the so called "French paradox". An analysis conducted on 34,014 men between 1978 and 1983 in Eastern France has shown that a moderate intake of wine (2–5 glasses of wine) was associated with a 24–31% reduction in all-cause mortality (Renaud S. C. et al., "Alcohol and Mortality in Middle-Aged Men from Eastern France", Epidemiology 9, 184–188, 1998).

Although many studies have been conducted with single antioxidant compounds, the pharmacological effects of the administration of the combination of antioxidant substances of natural origin as plant extracts of *Vitis vinifera* (Grape), of *Lycopersicon esculentum* (Tomato) with the vitamins C, E, beta-carotene and selenium have never been studied.

The Israeli Patent Application IL 121112 (Jun. 19, 1997) describes a synergistic mixture containing lycopene and vitamin E and its use in the prevention of LDL oxidation. The applicant also published the results in a scientific paper describing that the LDL protection by lycopene exceeded the protection by β-carotene. However, this effect was selective only to LDL's with high vitamin E content and was potentiated when the carotenoids were present in combination with vitamin E (Fuhrman B.; Ben-Yaish L.; Attias J.; Hayek T.; Avaram M., loc. cit.).

The U.S. Pat. No. 5,648,377 (Jul. 15, 1997) relates to the combination of lycopene with an extract of *Vitis vinifera* showing that the combination exerts a synergistic antioxidant action.

BRIEF SUMMARY OF THE INVENTION

The object of this invention is the surprising discovery that the administration of the combination of the extracts of the plants *Vitis vinifera* and *Lycopersicon esculentum* combined with vitamin C, vitamin E, β-carotene and optionally selenium significantly increases, in a synergistic manner, the cell protection. The results obtained from the described experimental tests show that the improvement of the cell protection with the combination of the mentioned substances are statistically greater than the combination of an extract of *Vitis vinifera* with lycopene (U.S. Pat. No. 5,648,377) or the combination of vitamin E with lycopene (IL Patent application 121112).

The invention therefore relates to a improved method of protecting the cell from a disease caused by an overproduction of free radicals, said method comprises administering a protective or therapeutically effective amount of a composition comprising synergistic amounts of a lipophilic antioxidant and a hydrophilic antioxidant and optionally an acceptable carrier, the improvement wherein is that said lipophilic antioxidant is a mixture consisting essentially of vitamin E, beta carotene and an extract of *Lycopersicum esculentum*, and said hydrophilic antioxidant is a mixture consisting essentially of vitamin C and an extract of *Vitis vinifera*.

In another aspect, the present invention provides a method of treating a subject suffering from a disease, which is caused by an overproduction of free radicals, comprising the administration of a therapeutically effective amount of a composition according to the present invention.

In a further aspect, the present invention provides a method of treating a subject suffering from an inflammation.

In another aspect, the method according to the present invention is applicable to the treatment of a subject suffering from atherosclerosis.

In yet another aspect, according to the invention there is provided a method for preventing the mutagenic activity induced by free radicals in a subject.

In still another aspect, the method of the present invention is useful for treating a subject suffering from a tumor.

DETAILED DESCRIPTION OF THE INVENTION

Figure 1:
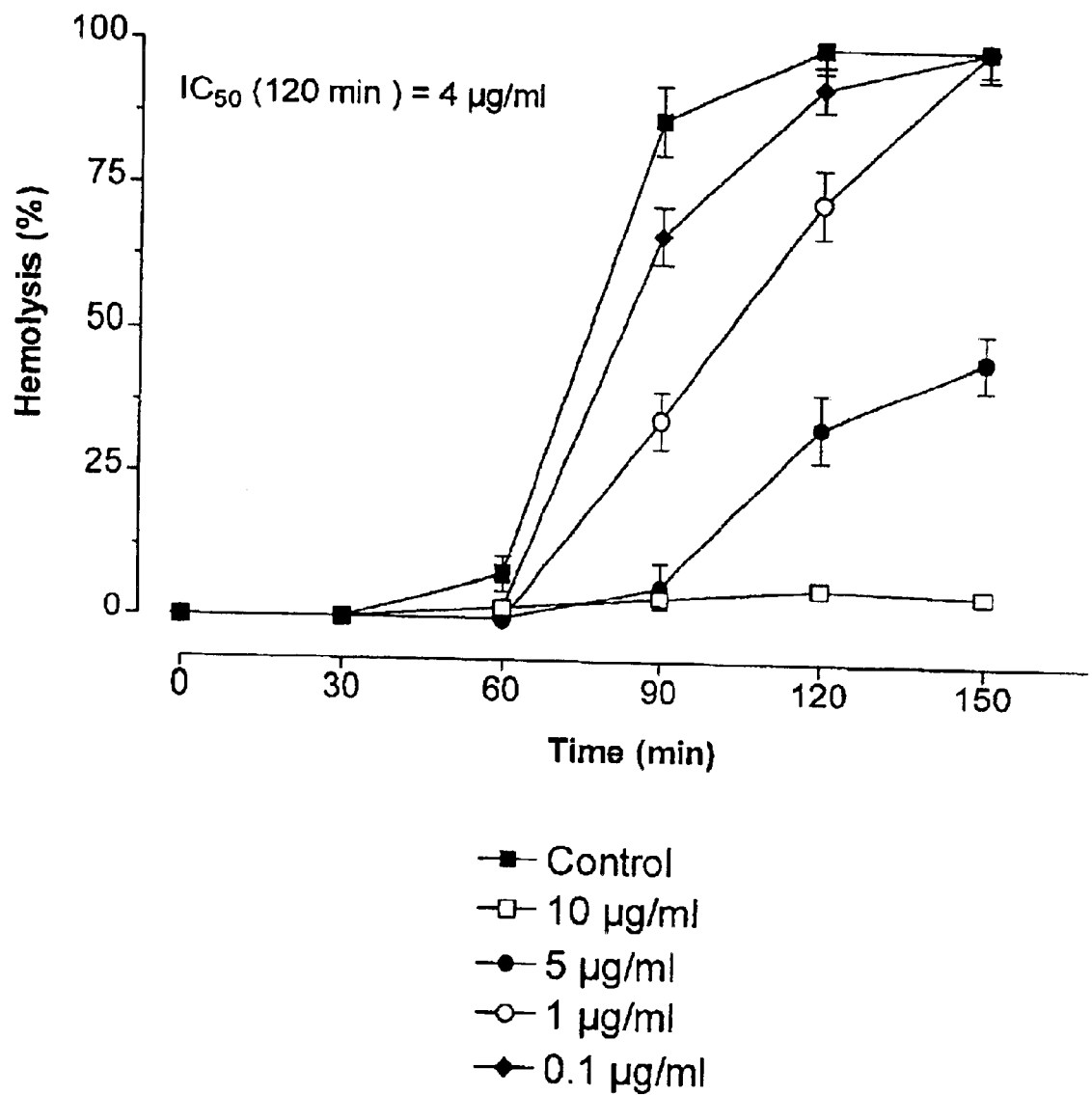
FIG. 1 shows the dose-dependent protective effect of the combination of the active ingredients on UVB-induced hemolysis (Example 1).

In a preferred embodiment the method according to this invention includes the administration of vitamin E, beta carotene, an extract of *Lycopersicum esculentum*, vitamin C, an extract of *Vitis vinifera* and a selenium compound. Preferred selenium compounds are sodium selenite or selenium yeast.

The term "extract of *Lycopersicum esculentum*" as used hereinabove or hereinbelow includes a dilute composition of lycopene. Said lycopene may be obtained by extraction from plants, algae, fungi or genetically modified organisms or by synthesis. Preferably the extract from dried skin of tomatoes is directly utilized.

The term "extract of *Vitis vinifera*" as used hereinabove or hereinbelow includes a dilute composition procyandolic oligomers. Preferably the extract from the seeds of red vines is directly utilized.

In another preferred embodiment the method according to this invention includes the administration of:
（a) 5 to 20 parts, preferably 7.5 to 15 parts of vitamin E, in particular vitamin E acetate or vitamin E succinate;
（b) 1 to 15 parts, preferably 2 to 10 parts of beta-carotene;
（c) 1 to 4 parts, preferably 1.5 to 3 parts of lycopene in the form of an extract of *Lycopersicum esculentum* obtained from dried skin of tomatoes.
（d) 2 to 60 parts, preferably 5 to 50 parts of vitamin C, in particular the sodium salt thereof; and
（e) 1 to 30 parts, preferably 1.1 to 25 parts of *Vitis vinifera* extract in particular obtained from the seeds of red vines.

Preferably the lipophilic antioxidant and the hydrophilic antioxidant are administered in the presence of a pharmaceutically acceptable carrier. Suitable excipients are exemplified in: Remington: the science and practice of pharmacy. 19th ed. Easton: Mack Publ., 1995.

Most preferred carriers are selected from the group consisting of natural plant oils, fully or partially hydrogenated plant oils, in particular soybean oil, fully or partially hydrogenated soybean oil, rape oil, peanut oil, lecithins, in particular soylecithin or egglecithin, plant phosphatides, in particular soyphosphatide and natural waxes, in particular beeswax.

The compositions may be formulated as solids or solutions. Solid formulations maybe for preparation of a solution before injection. Preferably, the pharmaceutical compositions of the invention are administered in the form of soft or hard gelatin capsule, tablet, coated tablet, suppository or in the transdermal form. The dosage will be adjusted according to factors like body weight and health status of the patient, nature of the underlying disease, therapeutic window of the compound to be applied, solubility, and the like. It is within the knowledge of the expert to adjust dosage appropriately.

Accordingly, a further aspect of the present invention is the use of a composition of the invention in the preparation of a pharmaceutical composition for the treatment of a subject suffering from pathological conditions being caused at least in parts to an overproduction of free radicals like aging, inflammation, atherosclerosis or cancer. Furthermore, an aspect of the invention is a method of prevention and/or treatment of inflammation, atherosclerosis or cancer, comprising administering an effective amount of a pharmaceutical composition of the invention to a patient.

The objective of this study was to evaluate first in rat erythrocytes the protective effect of the combination of the extracts of *Vitis vinifera, Lycopersicon esculentum*, vitamin C, vitamin E and beta-carotene against the UVB-induced damage and the existence of a cooperative interaction between its components, and then in keratinocytes cell lines the ability of selenium to increase the endogenous enzymatic antioxidant defenses.

In detail the following investigations have been carried out:
（a) the dose-dependent ability of the combination of the extract of *Vitis vinifera*, the extract of *Lycopersicon esculentum*, vitamin C, vitamin E and beta-carotene, thereafter denominated in this text as "combination of the active ingredients," to prevent hemolysis induced by large UVB doses (1.5–7.0 J/cm$^2$);
（b) the dose-dependent ability of a mixture of the lipophilic antioxidants (*Lycopersicon esculentum* extract, beta-carotene+vitamin E acetate) to inhibit hemolysis and lipid peroxidation in red cell membranes;
（c) the dose-dependent ability of a mixture of the hydrophilic antioxidants (*Vitis vinifera* extract and vitamin C) to inhibit hemolysis and lipid peroxidation in red cell membranes;
（d) the protective effect on hemolysis and lipid peroxidation in red cell membranes by the association of the mentioned lipophilic and hydrophilic antioxidants;
（e) the ability of selenium yeast to release selenium in a cellular system (keratinocytes): induction of glutathione peroxidase (GSH-PX) activity and cellular resistance to oxidative stress induced by physical (UVB) or chemical (cumene hydroperoxide) cytotoxic agents.

EXAMPLES

Materials and Methods

Chemicals

The organic solvents used in the experiments were of analytical grade (Carlo Erba, Milan, Italy). The active ingredients (*Vitis vinifera* extract, *Lycopersicon esculentum* extract, beta-carotene, lycopene, d,1-α tocopherol acetate, ascorbic acid, selenium yeast) were supplied by Pharmaton SA, CH 6934 Bioggio, Switzerland. Cumene hydroperoxide (CuOOH), thiobarbituric acid (TBA), EDTA, sodium selenite ($Na_2SeO_3$), sodium azide ($NaN_3$), sodium pyruvate, 2',7'-dichlorodihydrofluorescein diacetate (DCFH-DA), DMEM (Dulbecco's modified Eagle's medium), phenol red free DMEM, L-glutamine, penicillinstreptomycin solution were purchased from Sigma (Trimital, Milan, Italy); fetal calf serum and phosphate buffer solutions (PBS) from Hyclone (Belbio, Milan, Italy); $H_2O_2$ (30% v/v) from Fluka (Trimital, Milan, Italy); NADH, NADPH, GSH and GSH-reductase from Boehringer Mannheim Italy (Milan, Italy).

Apparatus

Spectrophotometric and fluorimetric studies were carried out in a computer-aided Perkin Elmer Lambda 16 spectrophotometer and a computer aided Perkin Elmer LS50B luminescence spectrometer (Perkin Elmer, Monza, Italy).

UVB Irradiation of Erythrocytes (RBC)

Erythrocytes from male Wistar rats (Charles River, Calco, Italy), isolated and washed from white blood cells and platelets were suspended in phosphate buffered saline, pH 7.4 (125 mM NaCl and 10 mM sodium phosphate buffer (PBS)), stored at 4° C. and used until 4 days old. For experiments, an aliquot of the erythrocyte suspension was drawn from the stock, centrifuged at 1000×g for 5 min and 0.1 ml of the pellet diluted to 50 ml with PBS obtain a 1% erythrocyte suspension (approximately 15×10$^7$ cells/ml).

50 ml aliquots of the RBC suspension were placed in Pyrex glass dishes (14 cm diameter) transparent to exciting-light wavelengths>290 nm and exposed to UBV radiation for different time intervals. When the inhibitors were added to the RBC suspension, a pre-incubation period of 30 min at 37° C. was applied. UVB radiation was carried out with a parallel bank of two Philips TL20W/12 fluorescence tubes (Sara s.r.l., Castellanza, Italy) emitting a continuous spectrum between 280 and 320 nm with a peak emission at 312 nm. Fluence rate at the site of cell irradiation (25 cm from UVB source) was of 0.85 mW/cm$^2$ and the UVB doses employed ranged from 1.5 to 7.0 J/cm$^2$ (exposure time 30–150 min), as measured with a Vilber Lourmat VLX-3W radiometer (UVB probe, 312 nm).

UVB-Induced Hemolysis

After irradiation, 2 ml aliquots of the RBC suspension were diluted 1:5 with buffered saline and hemolysis determined turbidimetrically at 710 nm at 30 min intervals for 180 min. Percentages hemolysis were determined setting as a 100% hemolysis the absorbance value determined in RBC suspensions sonicated for 5 sec at 50% power. Mean values of 5 determinations were used for calculation.

Keratinocytes

The NCTC 2544 human keratinocyte cell line (Flow Laboratories, Irvine, UK) was cultured at 37° C. in DMEM supplemented with 10% fetal calf serum 2 mM L-glutamine and antibiotics (100 U/ml penicillin and 0.1 mg/ml streptomycin). Cultures were maintained at 37° C. in a humidified 5% $CO_2$ atmosphere. For experiments, cells were seeded at a density of $5 \times 10^4/cm^2$ and cultured in 2 $cm^2$ cell plastic culture dishes until 80–90% confluence. Cell viability was determined by the trypan blue exclusion assay and by measuring the LDH leakage. Protein determinations were performed by a modified Lowry method, using bovine serum albumin as a standard.

Glutathione Peroxidase (GSH-PX) Activity

Cells grown were treated with sodium selenite (50, 500 nM) or selenium yeast (3.95 or 39.5 µg/ml corresponding to 50 and 500 nM Se) and incubated to 90% confluence (48 h). Before irradiation cell monolayers were washed three times with prewarmed PBS and exposed to UVB (50 mJ/$cm^2$), in the presence of PBS. After irradiation, PBS was replaced by serum-phenol red free DMEM (K-DMEM) and incubated for 24 h (sham-control cells were subjected to the same procedure without UV exposure). The media were discarded and the cells removed by gently scraping into 1 ml of 50 mM Tris-HCl buffer and lysed by sonication. The cellular suspensions (0.1 ml aliquots) were analysed for GPX activity by monitoring the decrease of absorbance at 340 nm for the rate of disappearance of NADPH in a thermostated (37° C.) spectrophotometer. GPX activity was calculated using a molar extinction coefficient of NADPH of $6.22 \times 10^3$ $cm^{-1}$ $m^{-1}$ and expressed as mU/mg protein, where 1 U of enzyme activity is defined as µmoles substrate consumed or product produced/min at 37° C.

CUOOH-Induced Oxidative Stress

The intracellular oxidative stress induced by CuOOH and the protective effect by selenium yeast was determined by measuring cell viability and peroxide content by using the oxidation-sensitive fluorescent probe DCF. Cells grown were treated with sodium selenite (50, 500 nM) or selenium yeast (3.95 or 39.5 µg/ml corresponding to 50 and 500 nM Se) and incubated to 90% confluence (48 h). Stock solution of DCFH-DA (3.34 mM) were prepared in ethanol, purged with nitrogen and stored at −20° C. in 500 µl aliquots. Cell monolayers were washed with prewarmed PBS and incubated with 10 µM DCFH-DA in PBS for 30 min at 37° C. Thereafter the medium was discarded and the cell monolayer washed three times with prewarmed PBS to remove not-incorporated DCFH-DA and then incubated with K-DMEM containing 0.5 mM CuOOH. Sham-control cells were subjected to the same procedure without CuOOH exposure. After 24 h incubation, the media were discarded and the cells removed by gently scraping into 3 ml of PBS. The cellular suspension was then transferred into 1 ml thermostated fluorescence cuvettes (25° C.) equipped with a magnetic stirrer and the increase of fluorescence intensity of the probe ($\lambda_{exc}$ 502 nm; $\lambda_{em}$ 520 nm; band widths 5 nm) recorded. The fluorescence intensity values at all the observation times were correlated to protein content (means±S.D. of 6 determinations) and expressed as % increase of fluorescence in respect to the controls (sham-control cells).

Statistical Analysis

Results are expressed as mean±S.D. of 5 independent determinations. Data were analysed by one-way analysis of variance (ANOVA), followed by the Tukey's test for statistical significance among groups and by Student's t-test (two tailed) for unpaired samples. Differences were considered significant when p<0.05. Statistical analysis was performed by using the Prism software package (GraphPad Software Inc., San Diego Calif., USA).

Example 1

Protective Effect of the Combination of the Active Ingredients

Exposure of rat RBC to increasing UVB doses gives the typical hemolysis curve reported in FIG. 1: the hemolytic process begins from 60 min irradiation, corresponding to an UVB dose of approximately 3 J/$cm^2$ (8.5±3.2%) and reached the plateau between 90 (87.2±6.3%) and 120 minutes (98.7±4.4%). The samples of the combination of active ingredients were prepared by mixing with PBS and vortexed; the homogenous suspension obtained was further diluted in PBS to final concentrations ranging from 0.1–10 µg/ml. When unirradiated RBC were incubated under aerobic conditions in the presence of the combination of active ingredients no significant hemolysis was observed within 3 h. The combination of active ingredients added to RBC suspension before irradiation, markedly and dose-dependently protected RBC from UVB-induced hemolysis (FIG. 1), with a minimal effective concentration of 0.1 µg/ml. At 5 µg/ml the hemolytic process was delayed by 30 min, and after 120 min irradiation the percentage hemolysis was only 34.5±5.5% and at the highest concentration (10 µg/ml) RBC integrity was maintained until 150 min UVB irradiation (7 J/$cm^2$). The $IC_{50}$ value, calculated at 120 min, was 4 µg/ml.

Example 2

Protective Effect of the Combination of Lipophilic and Hydrophilic Antioxidants of the Combination For a better understanding of the protective effect of the combination of the active ingredients on UVB-induced hemolysis, we have investigated the radical scavenging ability of a mixture of lipophilic (vitamin E acetate+beta-carotene+extract of *Lycopersicon esculentum*) and hydrophilic antioxidants (vitamin C+extract of *Vitis vinifera*).

Stock solutions of vitamin E acetate, beta-carotene and extract of *Lycopersicon esculentum* were prepared in THF under $N_2$ atmosphere and red light to prevent autooxidation and stored at −20° C. up to 1 week. The stability of each antioxidant was daily checked by UV spectroscopy. In order to maintain the same ratios between the antioxidants present in the combination of active ingredients, a mixed stock solution of 7.04 mg/ml for vitamin E acetate, 1.64 mg/ml for beta-carotene and of extract of *Lycopersicon esculentum* corresponding to 0.88 mg/ml lycopene was prepared by dilution with THF. A serial dilution was made to give the mixed lipophilic antioxidant working solutions at final concentrations of 1.2, 2.4, 4.8, 9.6 µg/ml of RBC suspension (total lipophilic antioxidants). In all the experiments THF concentration was always 0.1% (v/v).

The same approach was used for hydrophilic antioxidants: a mixed stock solution of vitamin C (6.72 mg/ml) and extract of *Vitis vinifera* (2.8 mg/ml) was prepared in PBS and a serial dilution was made to give the mixed hydrophilic antioxidant working solutions at 0.58, 1.16, 2.32, 4.64, 9.28 µg/ml RBC suspension (total hydrophilic antioxidants).

Figure 2:
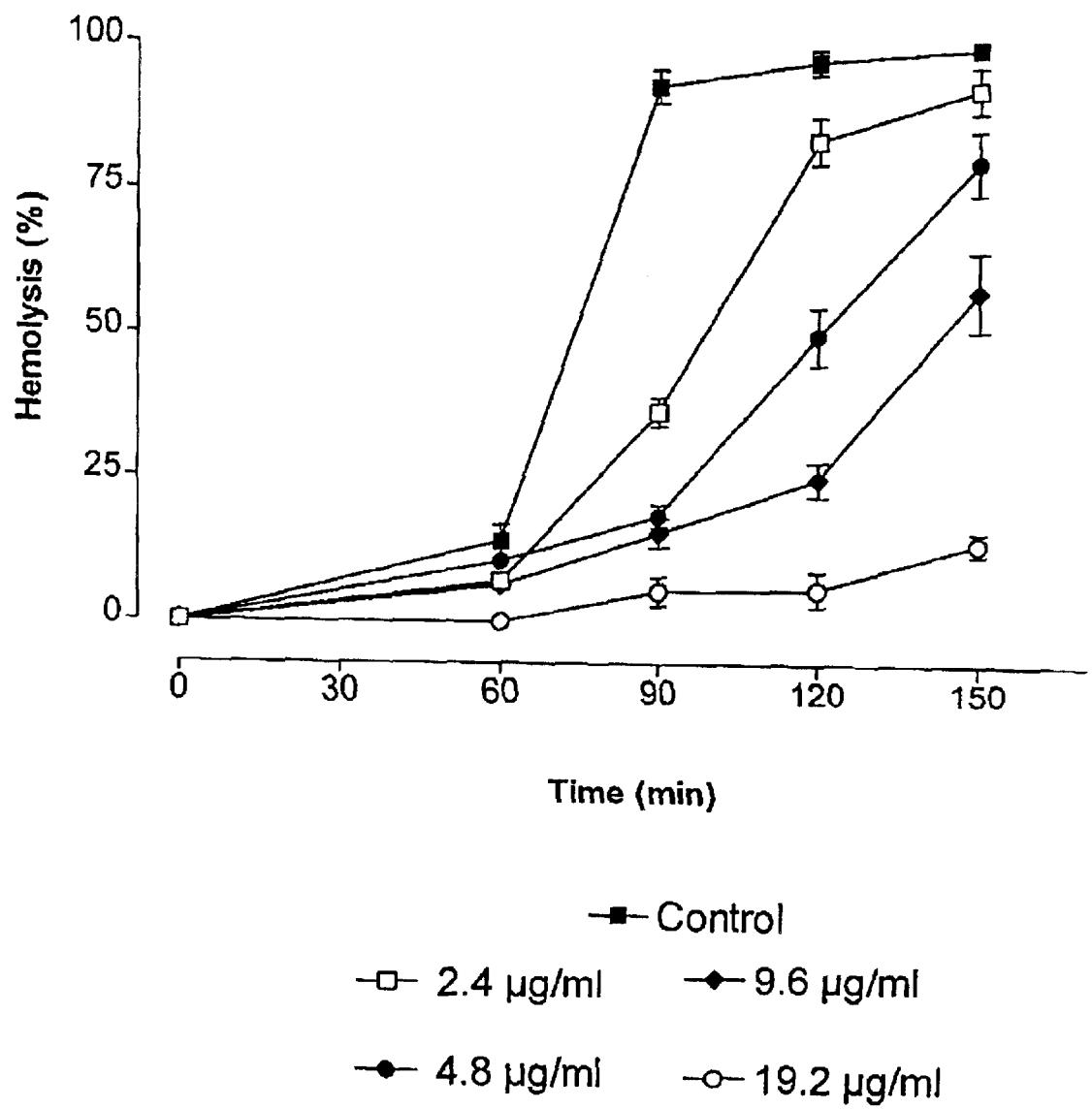
FIG. 2 shows the dose-dependent protective effect of lipophilic components of the combination of the active ingredients on UVB-induced hemolysis (Example 2).
Figure 3:
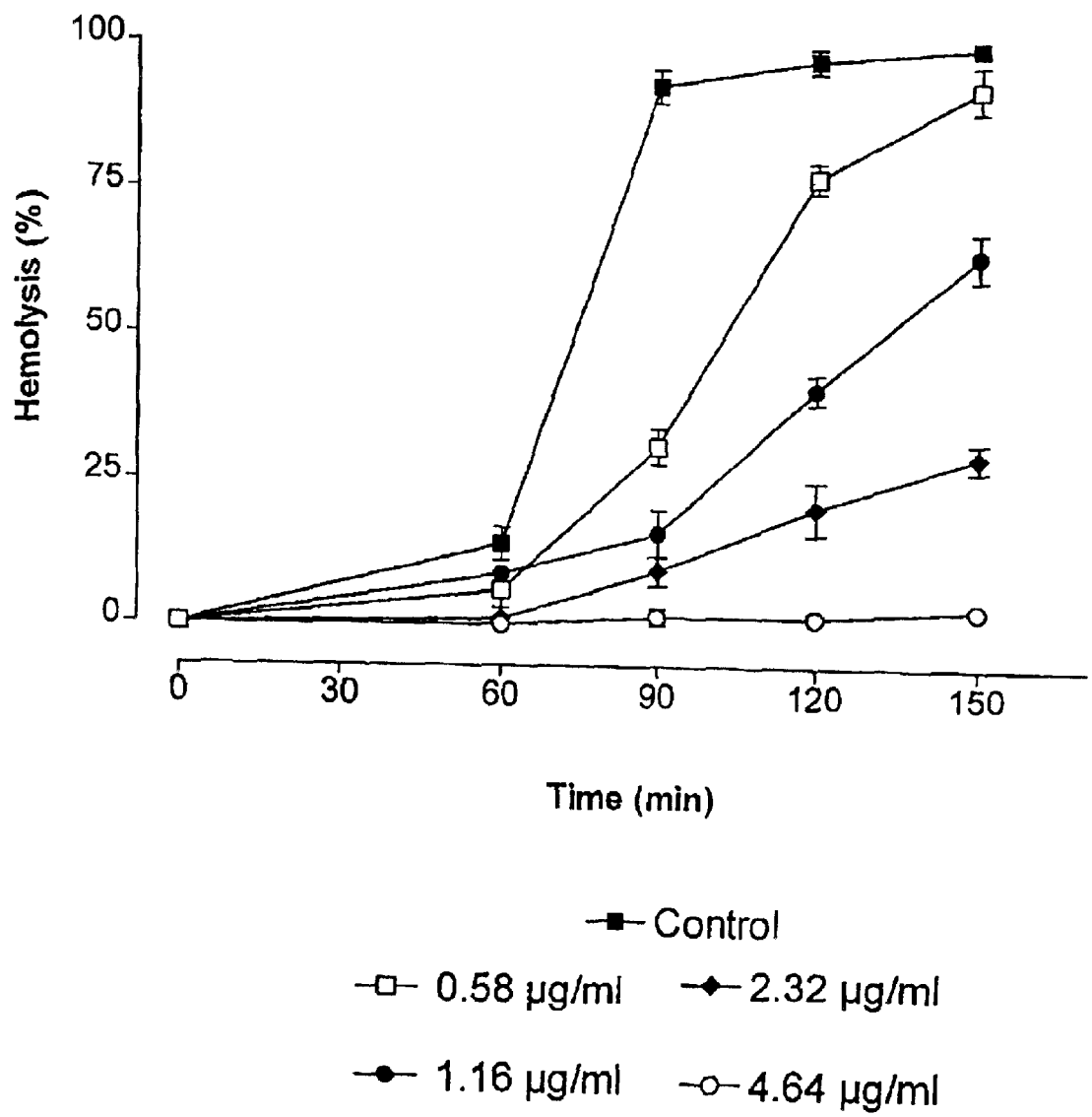
FIG. 3 shows the dose-dependent protective effect of hydrophilic components of the combination of the active ingredients on UVB-induced hemolysis (Example 2).

As shown in FIGS. 2 and 3, both the lipophilic and the hydrophilic fractions of the combination of active ingredients are able to prevent UVB-induced hemolysis, in a dose-dependent manner, although with different potency. The greater activity of the hydrophilic mixture is mainly due to the presence of the *Vitis vinifera* extract, which has been shown in different experimental models in vitro to be a potent chain-breaking antioxidant (Maffei Facino R.; Carini M.; Aldini G.; Bombardelli E.; Morazzoni P.; Morelli R., "Free radicals scavenging action and anti-enzyme activities of Procyanidines from *Vitis vinifera*—A mechanism for their capillary protective action", Arzneim. Forsch./Drug Res. 44, 592–601, 1994) and to save endogenous vitamin E from UVB-induced consumption, through recycling mechanism (hydrogen transferring reaction).

Figure 4:
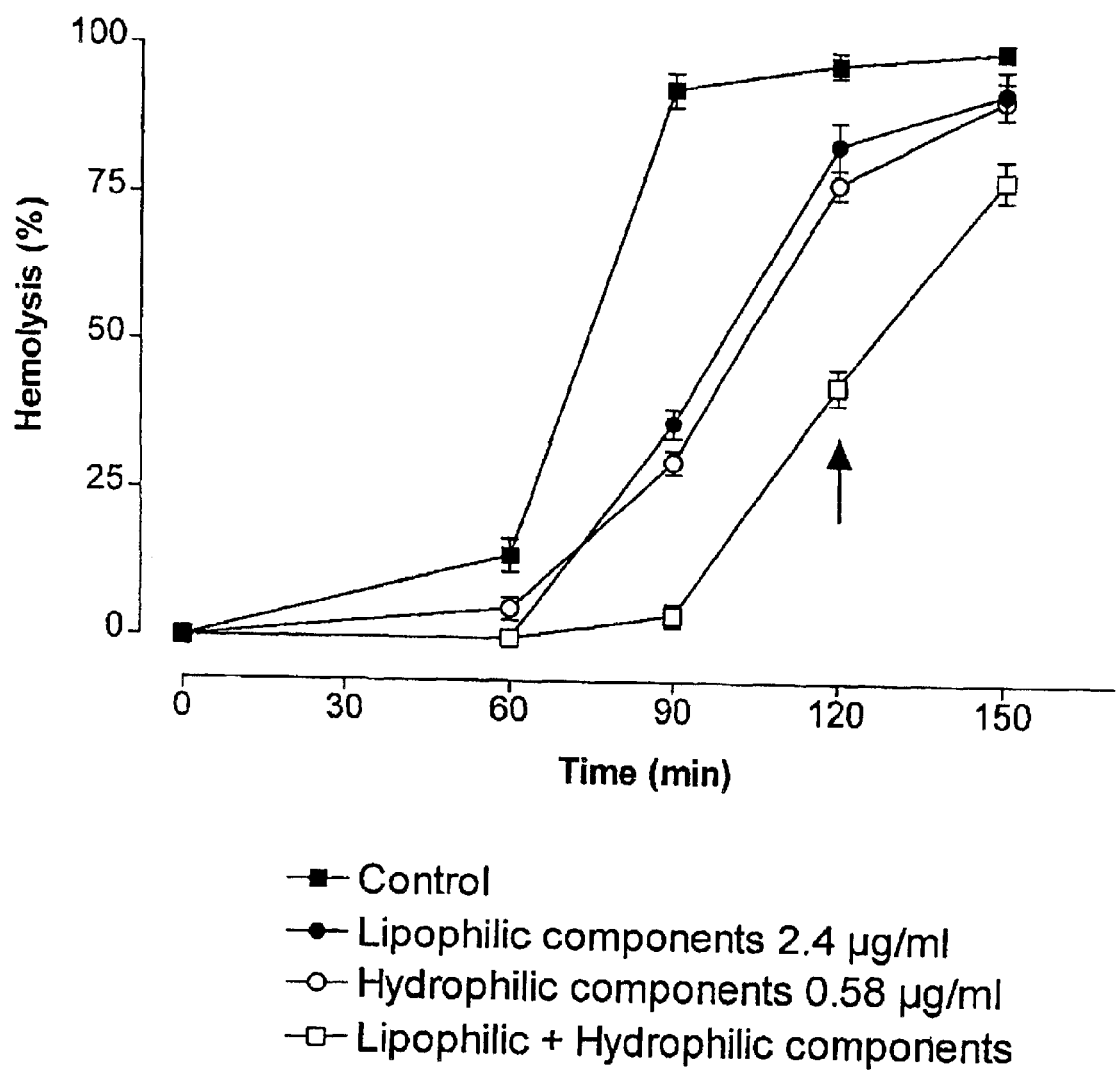
FIG. 4 shows the UVB-induced hemolysis: cooperative antioxidant interaction between lipophilic and hydrophilic components of the combination of the active ingredients (Example 3).
Figure 5:
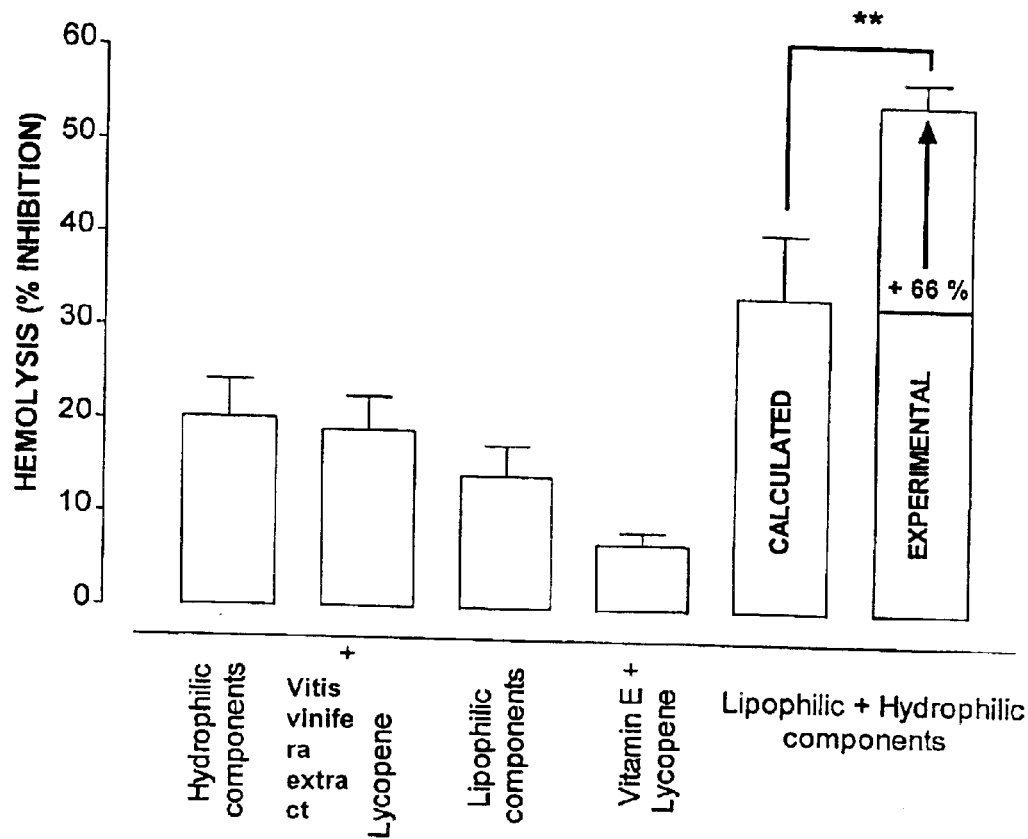
FIG. 5 shows the protective effect of the combination of the active ingredients on RBC hemolysis induced by 120 min irradiation (Example 3).

Example 3
Cooperative Antioxidant Interaction Between Lipophilic and Hydrophilic Antioxidants of the Combination The cooperative antioxidant interaction between lipophilic and hydrophilic antioxidants of the combination was studied by using concentrations of each mixed working solution that give approximately 20–30% inhibition at 120 min irradiation: 2.4 µg/ml for lipophilic (Vitamin E acetate 1.76 µg/ml, β-Carotene 0.41 µg/ml, lycopene 0.22 µg/ml) and 0.58 µg/ml for hydrophilic (Vitamin C 0.4 µg/ml, extract of *vitis vinifera* 0.18 µg/ml). The results are shown in FIGS. 4 and 5. Under these conditions, the rate of hemolysis was similar for both the mixtures, the hydrophilic being slightly more active than the lipophilic one (20% vs 14% inhibition at 120 min). When the antioxidants were combined, the rate of hemolysis was markedly slowered and the integrity of RBC was maintained up to 90 min. At 120 min the percentage inhibition (55±2.5%) was far beyond the sum of the % inhibitions (calculated:33.8%) observed with the individual antioxidant mixtures, to indicate a synergistic interaction. The protective effect elicited by a typical combination of hydrophilic/lipophilic antioxidants (*Vitis vinifera* extract+ lycopene) did not differ significantly from that observed with the combination of the hydrophilic ingredients (FIG. 5); by contrast, the association between vitamin E (1.76 µg/ml) and lycopene (0.22 µg/ml) gives a percentage inhibition of hemolysis significantly lower than that obtained with the combination of the lipophilic ingredients (7.1% vs 14%) (FIG. 5).

Figure 6:
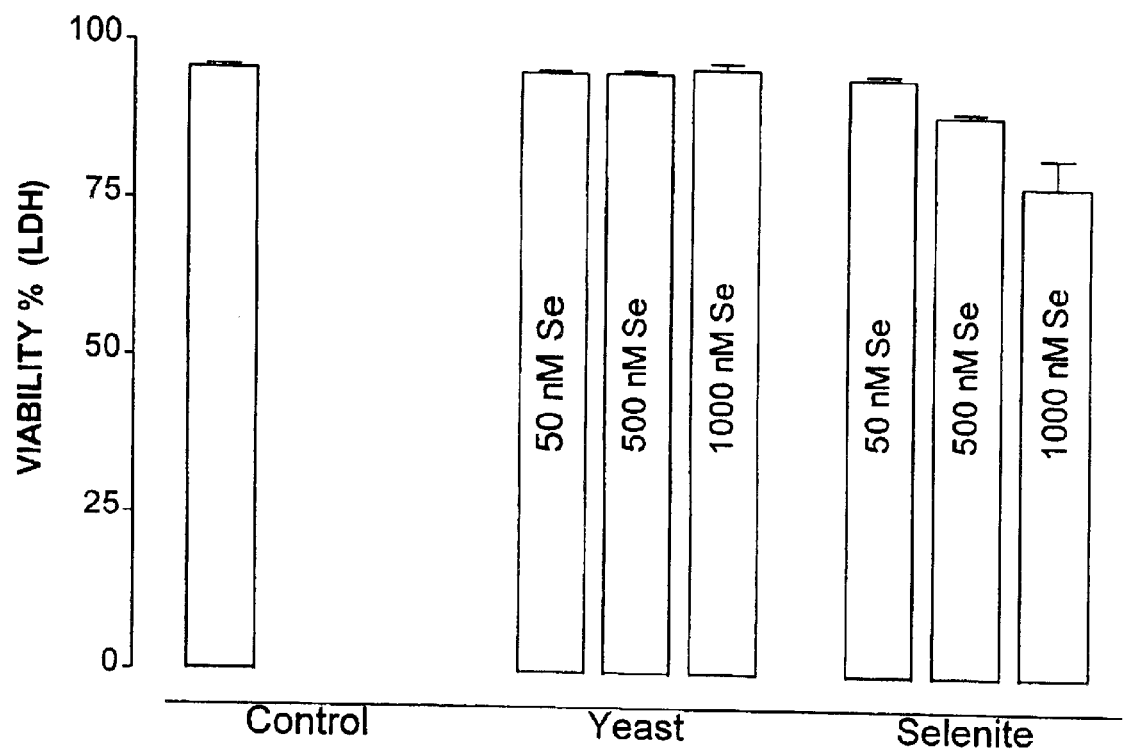
FIG. 6 shows the effect of selenium yeast and sodium selenite supplementation on keratinocytes viability (Example 4).

Example 4
Effect of Selenium Yeast Supplementation on Cell Growth and Cell Viability In cultured keratinocytes, sodium selenite or selenium yeast had no apparent growth-stimulating activity. Cell viability, determined LDH leakage (FIG. 6), was always over 95% and not significantly different in respect to the sham-control cells at 50 and 500 nM Se doses.

Example 5
Effect of Selenium Yeast Supplementation on GSH-PX Activity

Figure 7:
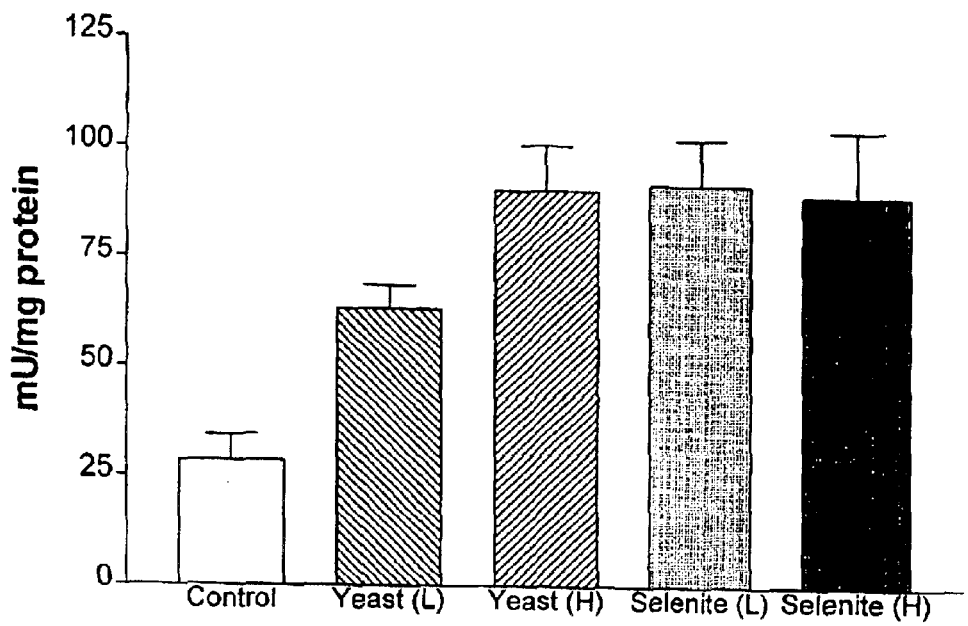
FIG. 7 shows the effect of selenium yeast and sodium selenite supplementation on keratinocyte glutathione peroxidase activity (Example 5).

FIG. 7 shows the effects of selenium yeast or sodium selenite supplementation (equimolar Se doses) in control cells: with sodium selenite maximal induction of GSH-PX activity was found at 50 nM (3.365 fold increase vs controls; 91.44±10.37 vs 28.31±5.87 mU/mg protein), and no further increase was observed at 500 nM concentration. Selenium yeast was less potent as GSH-PX inducer at the lower concentration (2.44-fold increase; 63.05±5.51 mU/mg protein), but at the concentration 39.5 µg/ml (corresponding to 500 nM Se) the increase in the enzymatic activity was comparable to that obtained with the equimolar dose of sodium selenite (90.11±10.35 mU/mg protein). These results clearly demonstrate that selenium yeast dose-dependently releases selenium for enzyme activation.

Figure 8:
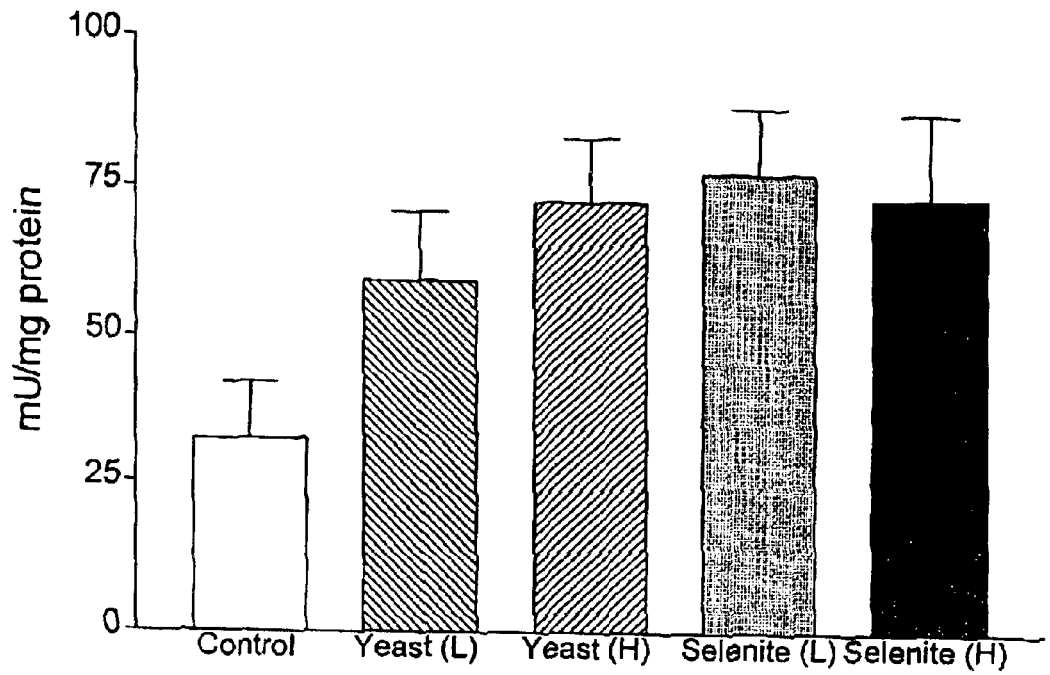
FIG. 8 shows the effect of selenium yeast and sodium selenite supplementation on glutathione peroxidase activity in keratinocytes exposed to UVB radiation (50 mJ/cm$^2$) (Example 5).

GSH-PX activity was also determined in keratinocytes exposed to UVB irradiation (50 mJ/cm$^2$), and the extent of enzyme induction by selenium yeast or sodium selenite was significantly enhanced in comparision to the control cells (FIG. 8), thus to indicate that also under oxidant imbalance selenium is still active.

Example 6
Effect of Selenium Yeast Supplementation on CuOOH-Induced Cell Death

Figure 9:
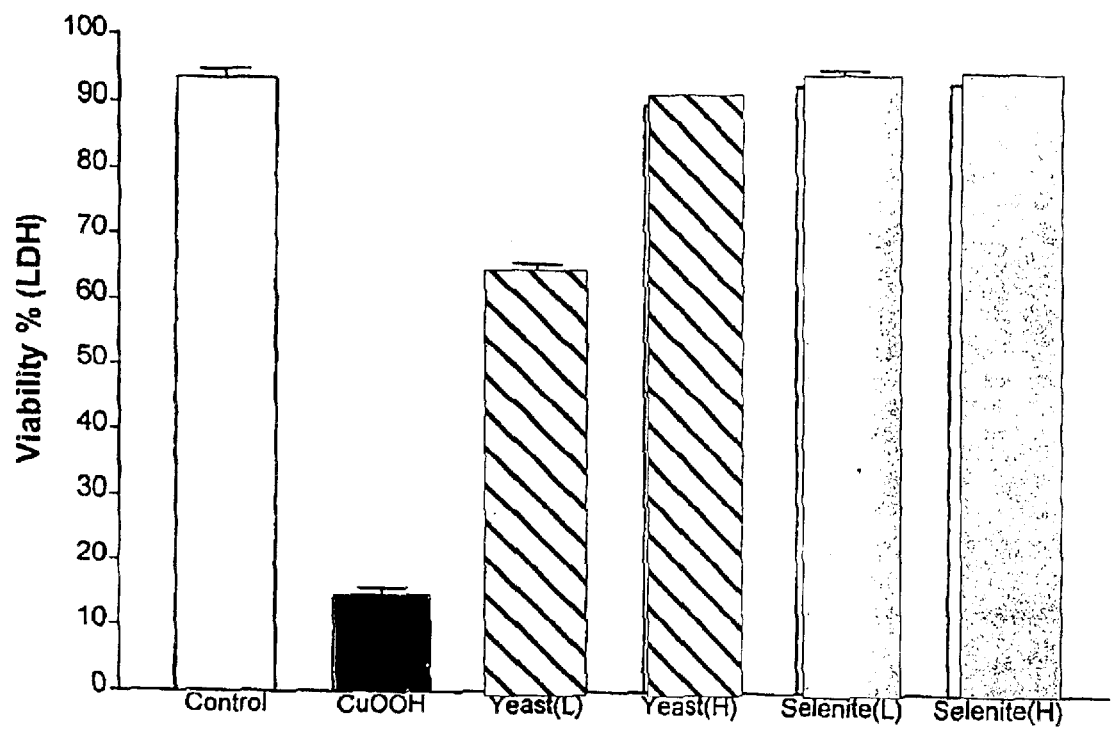
FIG. 9 shows the effect of selenium yeast and sodium selenite supplementation on cumene hydroperoxide (CuOOH)-induced cell death (Example 6).

Cumene hydroperoxide is a strong promoter of free radical reactions and incubation of keratinocytes with 500 µM CuOOH produced more than 80% cell death 24 h after exposure (FIG. 9). In selenium yeast-supplemented cells, cell death was markedly and dose-dependently restrained, cell viability being 64±1.3% at the lowest dose (3.95 µg/ml) and not significantly different from controls cells (90±1.2%) at the highest Se dose (39.5 µg/ml≈500 nM Se). The protection afforded by 50 nM sodium selenite was slightly greater, since cell viability was almost completely recovered.

Example 7
Effect of Selenium Yeast Supplementation on Intracellular CuOOH-Induced Oxidative Stress The intracellular oxidative status was determined by the sensitive fluorimetric DCF assay. The assay is based on the ability of the non-polar, non-fluorescent DCFH-DA to diffuse through the cell membrane and to be deacetylated by cytosolic esterases to form the polar, non-fluorescent dichlorodihydrofluorescein (DCFH). This last is trapped within the cytosol where, by reacting with reactive oxygen species generated by CuOOH, gives rise to the formation of the fluorescent derivative dichlorofluorescein (DCF).

Figure 10:
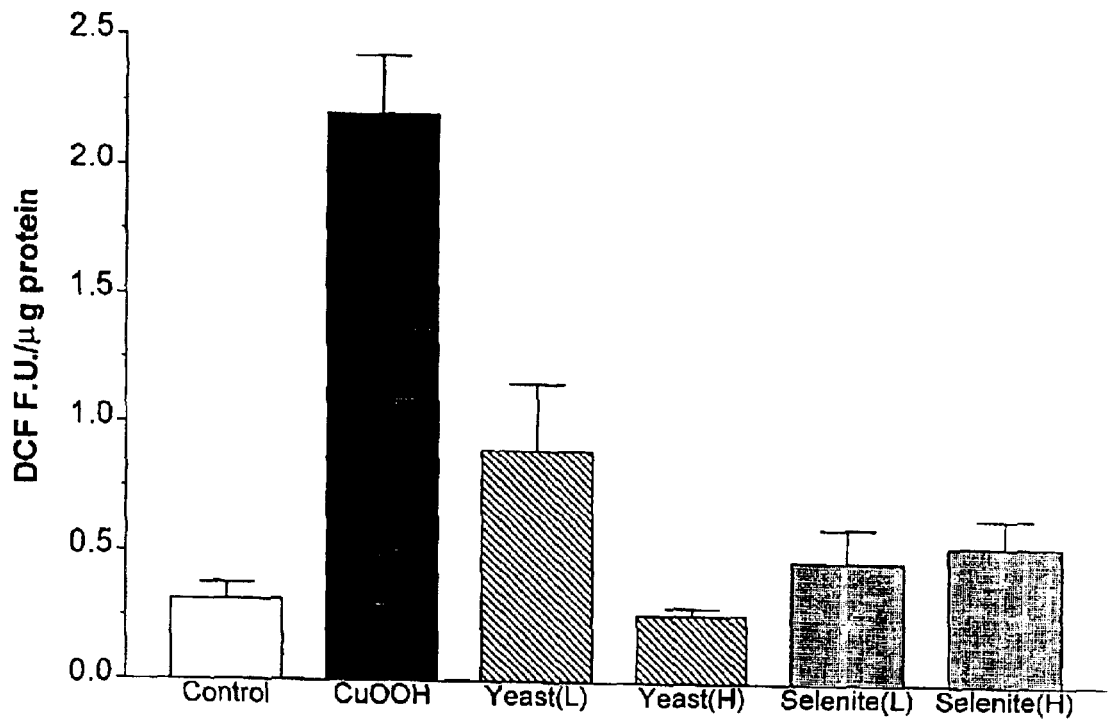
FIG. 10 shows the effect of selenium yeast and sodium selenite supplementation on CuOOH-induced intracelluar oxidative stress (DCF formation) (Example 7).

Incubation of keratinocytes with 500 µM CuOOH results in a significant accumulation of DCF (maximal after 24 h; more than 7-fold increase), to confirm the spreading of an oxidative burst in the cytosol compartment (FIG. 10). Pretreatment of the cells with selenium yeast counteracts the oxidative insult, since a 60% reduction of DCF formation was observed at the lower dose (3.95 µg/ml) and an almost complete protection at 39.5 µg/ml (550 nM Se). Sodium selenite totally prevents DCF formation already at the lowest dose (50 Nm).

These results of these examples indicate that it is the association between lipophilic and hydrophilic antioxidants, which is the object of the present invention that provides optimal cell protection against the oxidative challenge of UVB. In other words, there exists a synergistic interaction among antioxidants which explains the high degree of protection obtained with the combination of the active ingredients.

Since free radicals and reactive oxygen species (ROS) are generated in both the lipid and aqueous cell compartments, an antioxidant defense system as in the combination of the active ingredients, the object of the present invention, which can partition in both lipid and aqueous environments, is highly suited for cell protection.

Although the foregoing invention has been described in some detail by way of illustration and example for purposes of clarity of understanding, this invention is not limited to the particular embodiments disclosed, but is intended to cover all changes and modifications that are within the spirit and scope of the invention as defined by the appended claims.

All publications and patents mentioned in this specification are indicative of the level of skill of those skilled in the art to which this invention pertains. All publications and patents are herein incorporated by reference to the same extent as if each individual publication or patent application were specifically and individually indicated to be incorporated by reference.

What is claimed is:

1. A method of protecting a subject from a disease, or treating a subject suffering from a disease, wherein said disease is caused by an overproduction of free radicals, said method comprising administering to said subject a protective or therapeutically-effective amount of a composition consisting essentially of:
    (a) 5 to 20 parts of vitamin E;
    (b) 1 to 15 parts of beta carotene;
    (c) 1 to 4 parts of lycopene obtained from the extraction of dried skin of tomatoes;
    (d) 2 to 60 parts of vitamin C;
    (e) 1 to 30 parts of an extract of *vitis vinifera* from red vine seeds; and a pharmaceutically acceptable carrier.

2. The method of claim 1, wherein said disease caused by an overproduction of free radicals is selected from the group consisting of aging, inflammation, atherosclerosis, and cancer.

3. The method of claim 1, wherein said composition further comprises selenium.

4. The method of claim 1, wherein said vitamin E is vitamin E acetate or vitamin E succinate.

5. The method of claim 1, wherein said vitamin C is the sodium salt of vitamin C.

6. The method of claim 3, wherein said selenium is sodium selenite or selenium yeast.

7. The method of claim 1, wherein said pharmaceutically acceptable carrier is selected from the group consisting of natural plant oils, fully or partially hydrogenated plant oils, lecithins, plant phosphatides, and natural waxes.

8. The method of claim 1, wherein said pharmaceutically acceptable carrier is selected from the group consisting of soybean oil, fully or partially hydrogenated soybean oil, rape oil, peanut oil, soylecithin, soyphosphatide, egglecithin, and beeswax.

9. The method of claim 1, wherein said mixture is administered to said subject in the form of a soft or hard gelatin capsule, tablet, coated tablet, suppository, or in the transdermal form.

10. A method of protecting a subject from a disease, or treating a subject suffering from a disease, wherein said disease is caused by an overproduction of free radicals, said method comprising administering to said subject a protective or therapeutically-effective amount of a composition consisting essentially of:
    (a) 7.5 to 15 parts of vitamin E;
    (b) 2 to 10 parts of beta carotene;
    (c) 1.5 to 3 parts of lycopene obtained from the extraction of dried skin of tomatoes;
    (d) 5 to 50 parts of vitamin C;
    (e) 1.1 to 25 parts of an extract of *vitis vinifera* from red vine seeds; and a pharmaceutically acceptable carrier.

* * * * *